(12) United States Patent
Ng et al.

(10) Patent No.: US 11,610,688 B2
(45) Date of Patent: Mar. 21, 2023

(54) GENERATING PERSONALIZED TREATMENT OPTIONS USING PRECISION COHORTS AND DATA DRIVEN MODELS

(71) Applicant: International Business Machines Corporation, Armonk, NY (US)

(72) Inventors: Kenney Ng, Arlington, MA (US); Uri Kartoun, Cambridge, MA (US); Paul C Tang, Los Altos, CA (US); Charalambos Stavropoulos, Tarrytown, NY (US); Yoonyoung Park, Cambridge, MA (US); Amy Chiu, San Francisco, CA (US); Amarendra Das, Cambridge, MA (US)

(73) Assignee: MERATIVE US L.P., Ann Arbor, MI (US)

( * ) Notice: Subject to any disclaimer, the term of this patent is extended or adjusted under 35 U.S.C. 154(b) by 193 days.

(21) Appl. No.: 15/967,635

(22) Filed: May 1, 2018

(65) Prior Publication Data
US 2019/0341153 A1    Nov. 7, 2019

(51) Int. Cl.
G16H 50/70  (2018.01)
G16H 50/50  (2018.01)
G16H 20/00  (2018.01)

(52) U.S. Cl.
CPC ............. *G16H 50/70* (2018.01); *G16H 20/00* (2018.01); *G16H 50/50* (2018.01)

(58) Field of Classification Search
CPC ......... G16H 50/50; G16H 50/70; G16H 20/00
(Continued)

(56) References Cited

U.S. PATENT DOCUMENTS 6,081,786 A    6/2000  Barry et al.
7,593,952 B2   9/2009  Soll et al.
(Continued)

FOREIGN PATENT DOCUMENTS

WO    WO-2014052921 A2 *  4/2014  ......... G06F 19/3443
WO    2016036831           10/2016

OTHER PUBLICATIONS

Sharafoddini, A., Dubin, J. A., & Lee, J. (2017). Patient Similarity in Prediction Models Based on Health Data: A Scoping Review. JMIR medical informatics, 5(1), e7. https://doi.org/10.2196/medinform.6730. (Year: 2017).*

(Continued)

*Primary Examiner* — Joshua B Blanchette
*Assistant Examiner* — Winston Furtado
(74) *Attorney, Agent, or Firm* — Patterson + Sheridan, LLP

(57) ABSTRACT

A plurality of attributes are extracted from a plurality of electronic health records, where each electronic health record is associated with a patient in a plurality of patients. Additionally, a training data set and a scoring data set are generated based on the plurality of attributes, and a patient similarity model is trained based on the training data set. A precision cohort is identified, where the precision cohort includes patients in the plurality of patients from the scoring data set that are similar to a first patient based on an electronic health record of the first patient and the similarity model. At least one result statistic for each of a plurality of treatments given to patients in the precision cohort is determined, and a first treatment of the plurality of treatments is selected for the first patient based at least in part on the determined result statistics.

20 Claims, 7 Drawing Sheets

(58) Field of Classification Search
USPC .......................................................... 705/3
See application file for complete search history.

(56) References Cited

U.S. PATENT DOCUMENTS

| | | | |
|---|---|---|---|
| 7,809,660 | B2 | 10/2010 | Friedlander et al. |
| 9,697,099 | B2 | 7/2017 | Dubbels et al. |
| 9,734,289 | B2 | 8/2017 | Percora |
| 9,818,062 | B2 | 11/2017 | Clark et al. |
| 2002/0107707 | A1 | 8/2002 | Naparstek |
| 2009/0299766 | A1* | 12/2009 | Friedlander ............ G16H 50/20 705/3 |
| 2012/0185266 | A1 | 7/2012 | Trifunov |
| 2013/0085980 | A1 | 4/2013 | Alemi |
| 2013/0173342 | A1 | 7/2013 | Bills |
| 2013/0226612 | A1 | 8/2013 | Carmeli et al. |
| 2014/0279746 | A1* | 9/2014 | De Bruin ............. A61B 5/7267 706/12 |
| 2015/0026189 | A1* | 1/2015 | Li ........................ G06F 16/245 707/769 |
| 2015/0193583 | A1* | 7/2015 | McNair ................. G16H 50/20 705/2 |
| 2017/0132141 | A1 | 5/2017 | Allen et al. |
| 2017/0177822 | A1* | 6/2017 | Fogel ..................... G16H 50/20 |

OTHER PUBLICATIONS

Zhan et al. "Low-Rank Sparse Feature Selection for Patient Similarity Learning." Data Mining (ICDM), 2016 IEEE 16th International Conference on. IEEE, 2016.

Wang et al., "PSF: a unified patient similarity evaluation framework through metric learning with weak supervision." IEEE journal of biomedical and health informatics 19.3 (2015): 1053-1060.

Longhurst et al., "A 'Green Button' For Using Aggregate Patient Data At The Point of Care," doi: 10.1377/nlthaff.2014.0099; Health Affairs 33, No. 7 (2014): 1229-1235.

Becker et al, "Personalized Guideline-Based Treatment Recommendations Using Natural Language Processing Techniques," pp. 271-275 DOI 10.3233/978-1-61499-753-5-271.

Kenney Ng et al., "Personalized Predictive Modeling and Risk Factor Identification using Patient Similarity," IBM T. J. Watson Research Center, Year: 2015, pp. 1-5.

* cited by examiner

700

┌─────────────────────────────────────────────────────────┐
│ EXTRACT A PLURALITY OF ATTRIBUTES FROM A PLURALITY      │
│ OF ELECTRONIC HEALTH RECORDS, WHEREIN EACH              │ ~ 705
│ ELECTRONIC HEALTH RECORD IS ASSOCIATED WITH             │
│ A PATIENT IN A PLURALITY OF PATIENTS                    │
└─────────────────────────────────────────────────────────┘
                              ↓
┌─────────────────────────────────────────────────────────┐
│ GENERATE A TRAINING DATA SET AND A SCORING DATA         │ ~ 710
│ SET BASED ON THE PLURALITY OF ATTRIBUTES                │
└─────────────────────────────────────────────────────────┘
                              ↓
┌─────────────────────────────────────────────────────────┐
│ TRAIN A PATIENT SIMILARITY MODEL BASED ON               │ ~ 715
│ THE TRAINING DATA SET                                   │
└─────────────────────────────────────────────────────────┘
                              ↓
┌─────────────────────────────────────────────────────────┐
│ IDENTIFY A PRECISION COHORT OF PATIENTS IN THE          │
│ PLURALITY OF PATIENTS THAT ARE SIMILAR TO A FIRST       │ ~ 720
│ PATIENT BASED ON AN ELECTRONIC HEALTH RECORD            │
│ OF THE FIRST PATIENT AND THE SIMILARITY MODEL           │
└─────────────────────────────────────────────────────────┘
                              ↓
┌─────────────────────────────────────────────────────────┐
│ DETERMINE AT LEAST ONE RESULT STATISTIC FOR EACH        │
│ OF A PLURALITY OF TREATMENTS GIVEN TO PATIENTS          │ ~ 725
│ IN THE PRECISION COHORT                                 │
└─────────────────────────────────────────────────────────┘
                              ↓
┌─────────────────────────────────────────────────────────┐
│ SELECT A FIRST TREATMENT OF THE PLURALITY OF            │
│ TREATMENTS FOR THE FIRST PATIENT BASED AT LEAST         │ ~ 730
│ IN PART ON THE DETERMINED RESULT STATISTICS             │
└─────────────────────────────────────────────────────────┘

FIG. 7

GENERATING PERSONALIZED TREATMENT OPTIONS USING PRECISION COHORTS AND DATA DRIVEN MODELS

BACKGROUND

The present disclosure relates to data driven personalized treatment options, and more specifically, to generating dynamic precision cohorts based on cognitive similarity models.

When determining which treatment is best-suited for a particular patient, healthcare professionals often rely on guidelines associated with each treatment that describe characteristics of patients that make the treatment a good option, as well as characteristics that may make the particular treatment a poor option. In many instances, these treatment guidelines are derived based on randomized clinical trials. These guidelines are generic, and are not particularly useful to determine how effective the treatment will be for a particular specific patient. For example, the treatment guidelines may simply indicate that the treatment works best with patients that are older than 18 and younger than 65. Similarly, a treatment guideline for a particular medication may indicate that it does not work as well when the patient also takes another specified medication. Similarly, a given patient will frequently satisfy all of the guidelines for several treatments of the same disease or disorder. This makes it incredibly challenging to select a particular treatment, as the guidelines merely indicate whether the patient is eligible to receive the treatment, and there is no methodology to determine which will be most effective. Thus, existing methods are not sufficiently specific to enable personalized treatment options, and do not provide sufficient guidance for selecting between multiple treatment options which are all suitable based on the guidelines.

SUMMARY

According to one embodiment of the present disclosure, a method is disclosed. The method includes extracting a plurality of attributes from a plurality of electronic health records, wherein each electronic health record is associated with a patient in a plurality of patients. The method also includes generating a training data set based on the plurality of attributes, and generating a scoring data set based on the plurality of attributes. Additionally, the method includes training a patient similarity model based on the training data set. Further, the method includes identifying a precision cohort of patients in the plurality of patients that are similar to a first patient based on an electronic health record of the first patient and the similarity model. The method also includes determining at least one result statistic for each of a plurality of treatments given to patients in the precision cohort, and selecting a first treatment of the plurality of treatments for the first patient based at least in part on the determined result statistics.

According to a second embodiment of the present disclosure, a computer program product is disclosed. The computer program product comprises a computer-readable storage medium having computer-readable program code embodied therewith, and the computer-readable program code is executable by one or more computer processors to perform an operation. The operation includes extracting a plurality of attributes from a plurality of electronic health records, wherein each electronic health record is associated with a patient in a plurality of patients. The operation also includes generating a training data set based on the plurality of attributes, and generating a scoring data set based on the plurality of attributes. Additionally, the operation includes training a patient similarity model based on the training data set. Further, the operation includes identifying a precision cohort of patients in the plurality of patients that are similar to a first patient based on an electronic health record of the first patient and the similarity model. The operation also includes determining at least one result statistic for each of a plurality of treatments given to patients in the precision cohort, and selecting a first treatment of the plurality of treatments for the first patient based at least in part on the determined result statistics.

According to a third embodiment of the present disclosure, a system is disclosed. The system includes one or more computer processors and a memory containing a program which when executed by the one or more computer processors performs an operation. The operation includes extracting a plurality of attributes from a plurality of electronic health records, wherein each electronic health record is associated with a patient in a plurality of patients. The operation also includes generating a training data set based on the plurality of attributes, and generating a scoring data set based on the plurality of attributes. Additionally, the operation includes training a patient similarity model based on the training data set. Further, the operation includes identifying a precision cohort of patients in the plurality of patients that are similar to a first patient based on an electronic health record of the first patient and the similarity model. The operation also includes determining at least one result statistic for each of a plurality of treatments given to patients in the precision cohort, and selecting a first treatment of the plurality of treatments for the first patient based at least in part on the determined result statistics.

BRIEF DESCRIPTION OF THE SEVERAL VIEWS OF THE DRAWINGS

FIG. 7 is a flow diagram illustrating a method of generating personalized treatment options, according to one embodiment disclosed herein.

DETAILED DESCRIPTION

In embodiments disclosed herein, similarity models can be trained to dynamically generate a precision cohort for a particular patient based on patient data. Advantageously, these cohorts are significantly more personalized and predictive than groups or clusters that have been generated a priori. For example, existing methods may create a priori groups and simply assign each patient to the particular group. Embodiments disclosed herein, however, allow for the dynamic creation of a precision cohort that is specific to the actual patient seeking treatment. Further, in some embodiments, the precision cohort is specific to a particular disorder to be treated, such that a patient may have radically different precision cohorts for different disorders. In an embodiment, based on this precision cohort, the predicted efficacy of each potential treatment plan can be evaluated with respect to the individual patient, in order to inform the decision making process and ensure that the treatment option with the potential to be most effective is selected.

Figure 1:
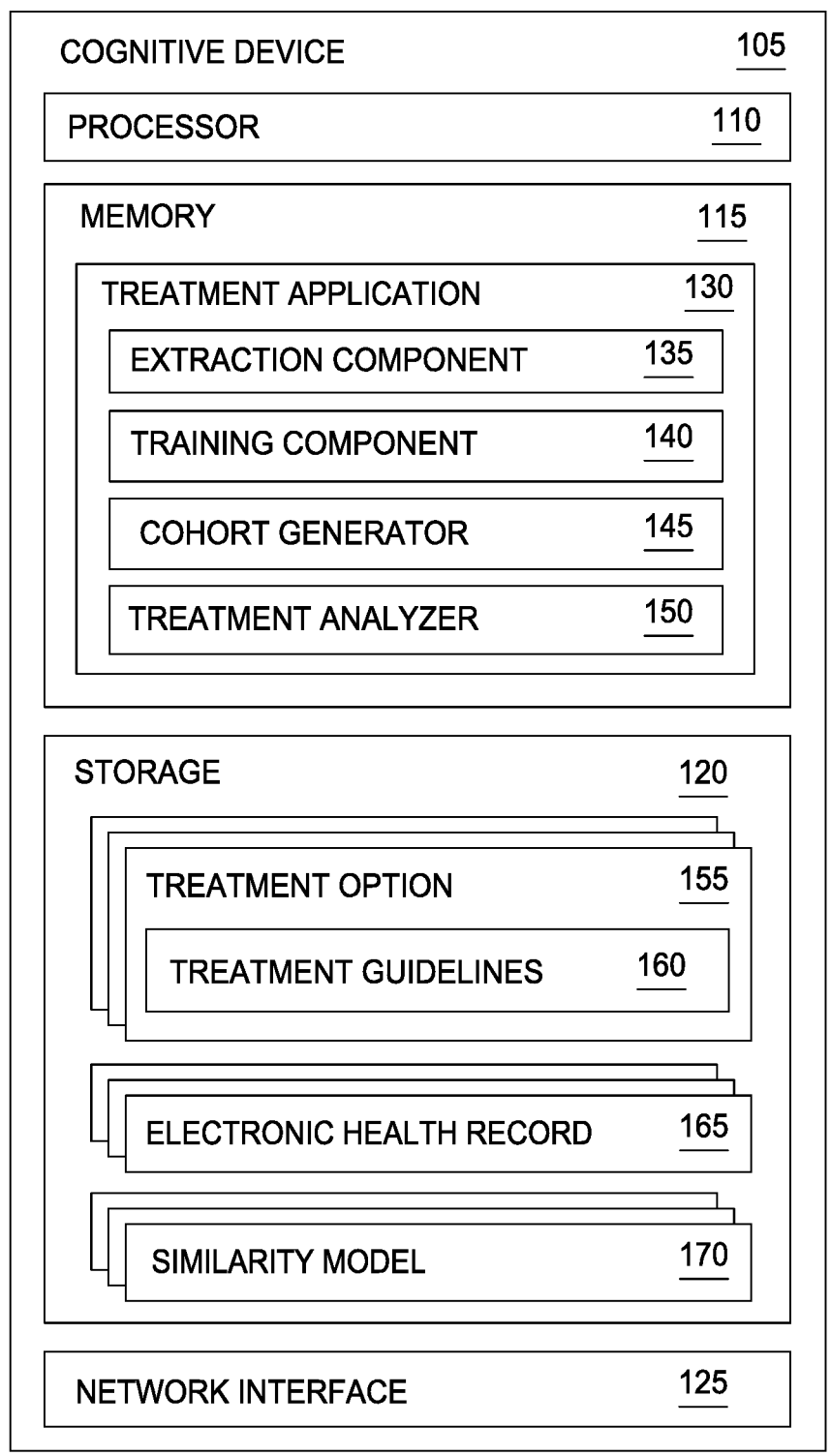
FIG. 1 is a block diagram illustrating a cognitive device configured to generate personalized treatment options, according to one embodiment disclosed herein.

FIG. 1 is a block diagram illustrating a Cognitive Device 105 configured to generate personalized treatment options, according to one embodiment disclosed herein. As illustrated, the Cognitive Device 105 includes a Processor 110, a Memory 115, Storage 120, and a Network Interface 125. In the illustrated embodiment, Processor 110 retrieves and executes programming instructions stored in Memory 115 as well as stores and retrieves application data residing in Storage 120. Processor 110 is representative of a single CPU, multiple CPUs, a single CPU having multiple processing cores, and the like. Memory 115 is generally included to be representative of a random access memory. Storage 120 may be a disk drive or flash-based storage device, and may include fixed and/or removable storage devices, such as fixed disk drives, removable memory cards, or optical storage, network attached storage (NAS), or storage area-network (SAN). In the illustrated embodiment, the Cognitive Device 105 may be communicatively coupled with other devices through the Network Interface 125.

The Memory 115 includes a Treatment Application 130. In an embodiment, the Treatment Application 130 analyzes treatment options to determine personalized plans for any particular patient at a particular point in time. As will be discussed below in more detail, this determination may be based in part on electronic health records of any number of patients. In the illustrated embodiment, the Treatment Application 130 includes an Extraction Component 135, a Training Component 140, Cohort Generator 145, and a Treatment Analyzer 150. In an embodiment, the Extraction Component 135 utilizes one or more natural language processing (NLP) models and techniques to extract various data from Electronic Health Records 165, which may include notes (e.g., clinical narrative notes), discharge summaries, magnetic resonance imaging (MM) data, computed tomography (CT) data, echocardiograms, EKG, biopsies, X-Ray reports, and the like. In some embodiments, the Extraction Component 135 also labels this extracted data to reflect what type of data it is, as will be discussed in more detail below. In one embodiment, the Training Component 140 receives this extracted data and generates one or more Similarity Models 170. In some embodiments, each Similarity Model 170 corresponds to a particular disease or disorder, and the Similarity Model 170 selected for generating the precision cohort varies depending on the disorder to be treated. In some embodiments, the precision cohort or the personalized treatment plan generated may also depend in part on genetic data derived from genome sequencing of each patient, as well as data captured via one or more wearable sensors (including ingestible sensors).

In an embodiment, the Cohort Generator 145 utilizes the Similarity Models 170 to generate a precision cohort for the patient for which the treatment options are being considered. The Treatment Analyzer 150 may then determine the predicted effectiveness of each option based on data associated with each patient in the precision cohort. In the illustrated embodiment, the Storage 120 includes a number of Treatment Options 155, each with one or more associated Treatment Guidelines 160. In embodiments, each Treatment Option 155 may include any plan for treating a disease or disorder. For example, a Treatment Option 155 may include one or more medications, diets, supplements, physical activities, and the like. In one embodiment, each Treatment Option 155 has been promulgated by professional entities based on research or clinical trials to treat the particular disorder. As used herein, a disorder refers to any medical condition, including but not limited to mental or physical disease, sickness, disability, infection, or status.

In some embodiments, each Treatment Option 155 may be associated with one or more Treatment Guidelines 160 that provide guidance on when the Treatment Option 155 should be used, based on the patient's demographics, comorbidities, medications, and the like. For example, one Treatment Guideline 160 may indicate that the Treatment Option 155 should not be used if the patient is younger or older than a predefined age. Other examples of Treatment Guidelines 160 include references to medications that should not be mixed, or an indication that the Treatment Option 155 should not be used if one or more other disorders are also present in the patient. In some embodiments, the Treatment Guidelines 160 may also include suggestions relating to the patient's demographic data such as race, gender, and the like. In an embodiment, these Treatment Guidelines 160 are also determined by organizations based on clinical trials and research. In some embodiments, the Treatment Guidelines 160 are binary. For example, one guideline may be "patient under 60" or "patient over 18." Similarly, a Treatment Guideline 160 may relate to whether the patient smokes, is obese, exhibits biometric data over or under a predefined threshold (e.g., blood pressure), and the like.

In the illustrated embodiment, the Storage 120 also includes a number of Electronic Health Records 165. Each Electronic Health Record 165 generally includes information relating to medical diagnoses, treatments, symptoms, disorders, and the like for a particular patient. In some embodiments, each patient has a single Electronic Health Record 165 that includes their medical information across a period of time. In some embodiments, each patient may have multiple Electronic Health Records 165. For example, in one embodiment, an Electronic Health Record 165 may include information relating to an appointment with a healthcare provider (e.g., the reason for the visit, symptoms presented, diagnosis, lab reports ordered and the associated results, and the like), while a second Electronic Health Record 165 may include information relating to a different appointment, lab test, specialist referral, and the like. Similarly, in one embodiment, information regarding a single appointment may be found in multiple Electronic Health Records 165, or information regarding multiple appointments may be located in a single Electronic Health Record 165. In an embodiment, the Electronic Health Records 165 may include structured and/or unstructured data. For example, structured data may be organized or labeled (such as an "age" field in a document), while unstructured data may include text without any labeling (such as a section where a patient describes his symptoms, or a doctor records her hypothesis or diagnosis).

As illustrated, the Storage 120 also includes Similarity Models 170 which have been generated by the Training Component 140, as will be discussed in more detail below. In one embodiment, each Similarity Model 170 is associated with a particular disorder. This may ensure that the precision cohorts are generated with increased specificity for the particular disorder to be treated. That is, rather than utilizing a priori groupings based on things like patient demography and comorbidities, in one embodiment, the Similarity Models 170 are disorder-specific such that the resulting precision cohort is tailored to the particular disorder, in addition to being dynamically tailored to the particular patient. Advantageously, this ensures more specialized models and more accurate predictions regarding treatment efficacy.

Figure 2:
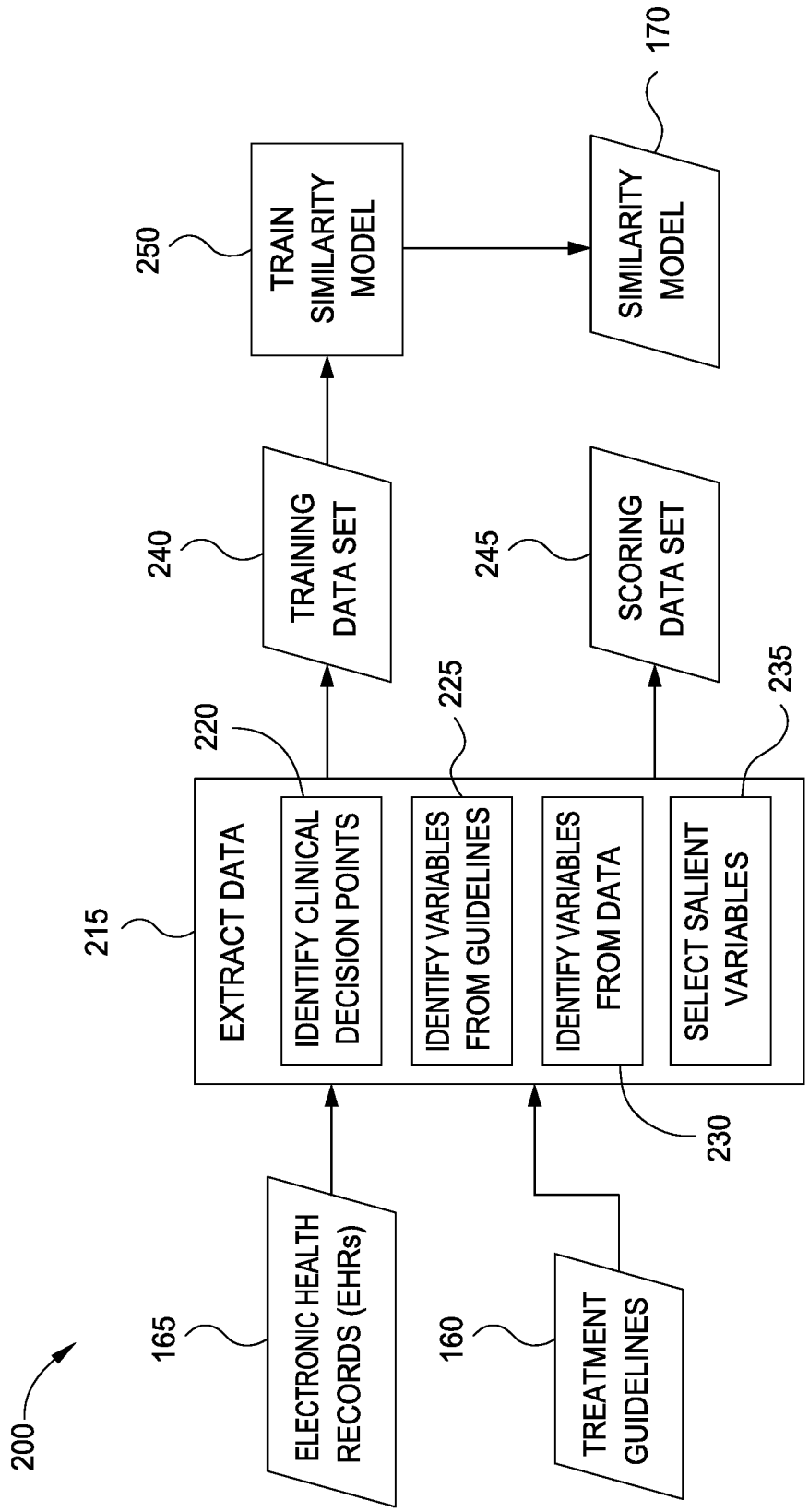
FIG. 2 illustrates a cognitive architecture for generating similarity models based on health records, according to one embodiment disclosed herein.

FIG. 2 illustrates a cognitive architecture 200 for generating Similarity Models 170 based on health records, according to one embodiment disclosed herein. In the illustrated embodiment, Electronic Health Records 165 and Treatment Guidelines 160 are provided to the Extraction Component 135. In an embodiment, these Electronic Health Records 165 may include data associated with any number of patients. In one embodiment, prior to being processed, each Electronic Health Record 165 is anonymized to remove any identifying information. In this way, patient privacy is maintained. In one embodiment, the Electronic Health Records 165 correspond to a particular disorder. For example, as discussed above, in some embodiments a separate Similarity Model 170 is generated for each disorder. In such an embodiment, the Electronic Health Records 165 provided to the Extraction Component 135 may correspond to a particular disorder for which the Similarity Model 170 is being generated. For example, the Electronic Health Records 165 may include information about diagnosis and treatment of the particular disorder from any number of patients and healthcare providers, at any number of points in time. In some embodiments, the Electronic Health Records 165 may include information relating to any number of disorders. In such an embodiment, the Treatment Application 130 may determine which disorder(s) are represented in each record, and ensure that each Similarity Model 170 is trained using data associated with the particular disorder(s). In the illustrated embodiment, the Treatment Guidelines 160 generally include the guidelines related to the various Treatment Options 155 for the particular disorder being trained.

As illustrated by block 215, the Extraction Component 135 identifies and extracts various types of data from the Electronic Health Records 165. For example, in the illustrated embodiment, at block 220 the Extraction Component 135 identifies clinical decision points in the Electronic Health Records 165. As used herein, a clinical decision point is a point in time where a healthcare provider made a decision regarding treatment of a patient. For example, when a patient attends an appointment with a healthcare provider, a clinical decision point is likely to be identified because the provider will likely consider what treatment plan to proceed with. In some embodiments, along with identifying clinical decision points, the Extraction Component 135 may also identify the treatment option selected by the healthcare provider at each moment. In embodiments, these options may include no change in the plan, as well as prescribing or removing medications, diets, supplements, physical activities, and the like. In some embodiments, multiple clinical decision points may be associated with a single patient. For example, when training a Similarity Model 170, a clinical decision point may be identified for the initial diagnosis of the disorder for a first patient, a corresponding specialist referral for the first patient, a checkup for the first patient after some time on the selected treatment plan, and so on.

In the illustrated embodiment, at block 225, the Extraction Component 135 identifies guideline variables in the Treatment Guidelines 160. In some embodiments, these extracted guideline variables also include an indication of the corresponding value. For example, a guideline variable may be that patient age should be greater than or equal to 18 in order for the associated Treatment Option 155 to be used. At block 230, the Extraction Component 135 also extracts and identifies data variables from the Electronic Health Records 165, such as attributes of the patient associated with each Electronic Health Record 165. In various embodiments, these attributes may include demographic data of the patient, symptoms, comorbidities, and the like. In some embodiments, the attribute variables are extracted in relation to each identified clinical decision point. For example, in some embodiments, each clinical decision point may be associated with corresponding attribute variables of the patient at that time. In some embodiments, the Extraction Component 135 also identifies and extracts results data for each clinical decision point. For example, the Extraction Component 135 may determine whether a decision made at a first clinical decision point led to the disorder being controlled or eliminated, the magnitude of the change, and the how long it took for the change to be realized.

At block 235, the Extraction Component 135 selects the most salient variables from the guideline variables and data variables (e.g., patient attributes) extracted from the Electronic Health Records 165. For example, in some embodiments, the Extraction Component 135 may identify hundreds or thousands of variables in the Treatment Guidelines 160 and Electronic Health Records 165. In an embodiment, the Extraction Component 135 uses one or more feature selection techniques, algorithms, or models to identify which variables are the most salient, and which are duplicative or irrelevant. These feature selection methods may include univariate or multivariate approaches, and may correspond to any suitable methodology of selecting the most salient or relevant features for the model, including filter methods, wrapper methods, embedded methods, model driven approaches, and the like.

In the illustrated embodiment, in blocks 240 and 245, the Extraction Component 135 also generates a Training Dataset 240 and a Scoring Dataset 245 using the extracted variables (or using the variables determined to be salient). In some embodiments, the Training Dataset 240 and Scoring Dataset 245 may not overlap. In other embodiments, however, the Training Dataset 240 and Scoring Dataset 245 may overlap. For example, in one embodiment, the Scoring Dataset 245 is a subset of the Training Dataset 240. In another embodiment, the Training Dataset 240 may be a subset of the Scoring Dataset 245. In one embodiment, the Training Dataset 240 includes a row for each identified clinical decision point. Each row may include multiple data variables determined to be salient (such as a patient's demographic details, laboratory measurements, comorbidities, medications, and additional characteristics such as smoking status, alcohol use, as well as other health behaviors and social determinants of health). The Training Dataset 240 may also contain an outcome data element, denoted as the "label" for each row. In an embodiment, each row in the training set contains values for the variables (if available) and a label value. The data may contain multiple rows per patient, representing multiple care encounters (i.e., multiple clinical decision points) across time. For example, a first row in the Training Dataset 240 may include information corresponding to a first healthcare encounter by a first patient, while a second row includes information about a second encounter by the first patient and a third row includes information about a first encounter by a second patient.

In one embodiment, the Scoring Dataset 245 similarly includes rows of data like the Training Dataset 240, but may also include additional variables that are excluded from the Training Dataset 240. In some embodiments, one or more variables may not be determined to be salient for training the Similarity Model 170, but they may still be useful for other purposes. For example, the Scoring Dataset 245 may include additional variables to be displayed to users (e.g., healthcare providers) to provide additional context. In an embodiment, these additional variables are thereby provided to the healthcare provider for consideration, without being used to affect the selection, scoring, or filtering of the precision cohort. Similarly, in some embodiments, the Scoring Dataset 245 may include additional patients or a different set of patients that are not included within the Training Dataset 240. In some embodiments, the Scoring Dataset 245 may be updated more frequently to include new information (e.g., new rows or new patients), while the Training Dataset 240 may updated less frequently. For example, in one embodiment, the Scoring Dataset 245 is updated whenever new information is available, while the Training Dataset 240 may be periodically updated, along with the Similarity Models 170.

In an embodiment, once the Training Dataset 240 has been created, the Training Component 140 trains a Similarity Model 170 based on this dataset, as depicted by block 250 in the illustrated embodiment. In various embodiments, the Similarity Model 170 may be trained using a variety of methods, such as locally supervised metric learning (LSML) or one or more clustering algorithms. In an embodiment, training the Similarity Model 170 comprises learning a weight matrix that aligns similar patients (i.e., those with the same outcome label value) more closely together, and disparate patients (those with different outcome label values) further apart in a high-dimensional vector space. Using this trained Similarity Model 170, when a new patient is to be treated, similar patients can be identified, as will be discussed in more detail below.

Figure 3:
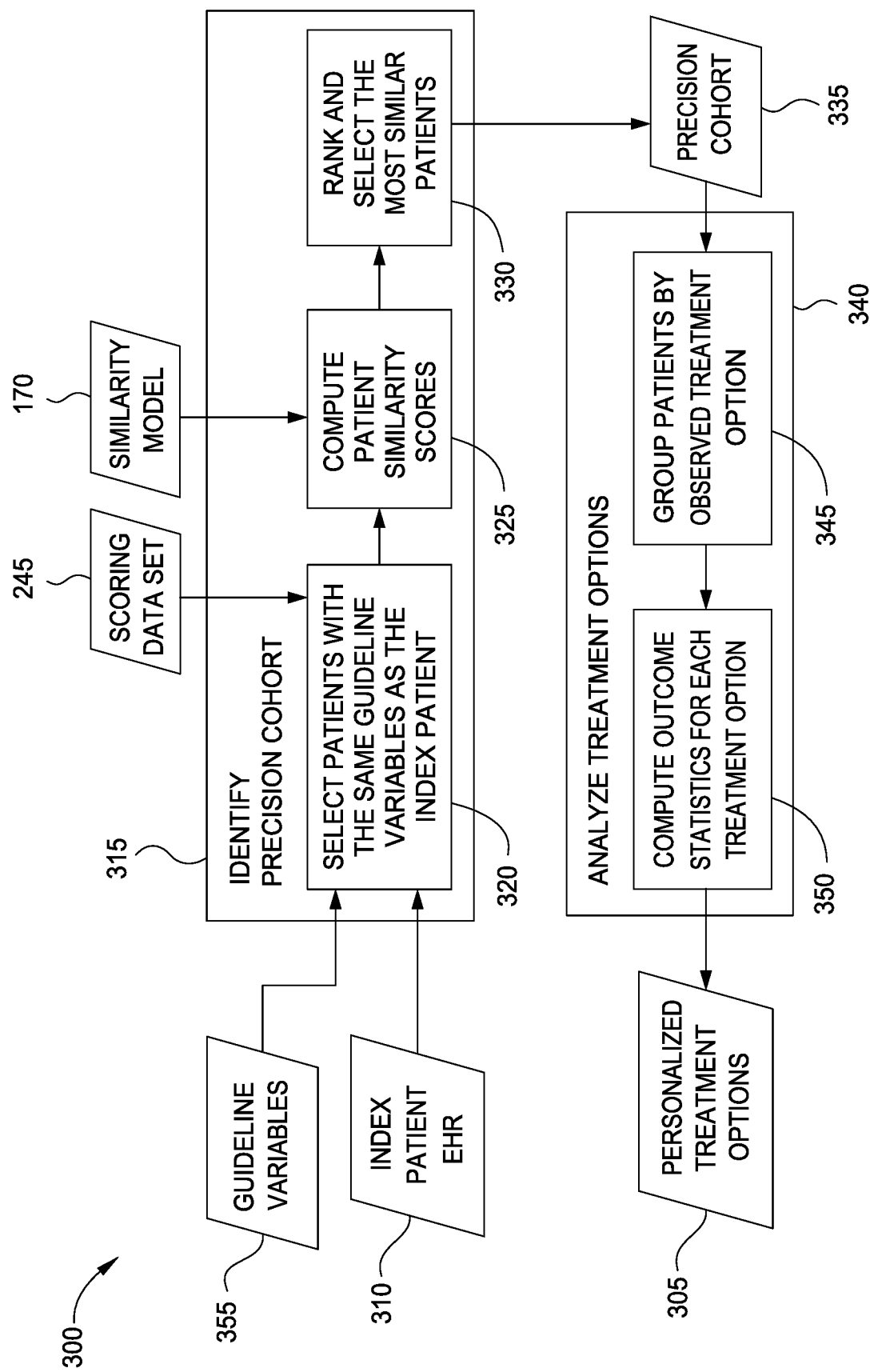
FIG. 3 illustrates a cognitive architecture for generating personalized treatment options, according to one embodiment disclosed herein.

FIG. 3 illustrates a cognitive architecture 300 for generating personalized treatment options, according to one embodiment disclosed herein. In the illustrated embodiment, the Cohort Generator 145 receives the Scoring Dataset 245, Similarity Model 170, and one or more Electronic Health Records 310 corresponding to the particular patient being treated (e.g., the "index patient"), and generates a Precision Cohort 335, as illustrated in block 315. As illustrated, the Cohort Generator 145 may also receive the identified Guideline Variables 355 in the Treatment Guidelines 160 such as a "is 60 or older" variable, a "is a smoker" variable, a "is obese" variable, and the like. At 320, the Cohort Generator 145 first selects patients in the Scoring Dataset 245 (e.g., rows in the Scoring Dataset 245) with guideline variables that align with the index patient. For example, if one guideline variable is "is 60 or older" and the index patient is thirty, the Cohort Generator 145 will only select rows in the Scoring Dataset 245 that include a variable indicating that the corresponding patient is also younger than sixty. A similar operation is completed for each identified guideline variable, such that a subset of the Scoring Dataset 245 is generated, where each patient in the subset of patients exhibits the same attributes as the index patient with respect to the identified guideline variables.

Once this subset has been generated, at block 325, the Cohort Generator computes similarity scores for each patient (e.g., each row) in the subset using the generated Similarity Model 170 corresponding to the disorder that is to be treated. In various embodiments, this similarity score may be a value between zero and one, a percentage, and the like. Generally, the similarity score indicates how similar the patients are based on the myriad of attributes identified and extracted by the Extraction Component 135. At block 330, the Cohort Generator then ranks the rows in the Scoring Dataset 245, and selects the most similar rows based on this generated similarity score in order to create the Precision Cohort 335. In some embodiments, the Cohort Generator 145 may select all patients (e.g., all rows) with a similarity score exceeding a predefined threshold. In some embodiments, the Cohort Generator 145 selects the N rows with the highest similarity measures, where N is a predefined value. In some embodiments, a covariate balance is computed based on the patients included in the Precision Cohort 335, and additional patients (or rows) are added based on their similarity measures until the covariate balance exceeds a threshold, indicating that the precision cohort is no longer homogenous enough. Advantageously, the Precision Cohort 335 is generated dynamically based on the individual index patient. This allows for highly personalized treatment plans which better predict the efficacy of various options.

In block 340, the Treatment Analyzer 150 determines a predicted efficacy of each treatment option, based on result statistics from the Precision Cohort 335. In an embodiment, as illustrated in block 345, the Treatment Analyzer 150 groups the patients (e.g., rows of data) based on the treatment option that was selected at the identified clinical decision point corresponding to the row. That is, each group may include information about each row of data or patient (e.g., each clinical decision point) in the precision cohort 335 where the healthcare provider selected a particular treatment plan. At block 350, the Treatment Analyzer 150 can then compute an outcome or result statistic for each of the treatment options, based on the precision cohort. That is, for each patient (or row of data) in a group corresponding to a particular treatment option, the Treatment Analyzer 150 may determine whether the treatment was successful in mitigating or controlling the disorder, how long it took before the disorder was under control, and the like. These results can be aggregated to generate an overall result statistic for the treatment option based on the precision cohort. For example, suppose the precision cohort includes four thousand individual rows of data (which may correspond to four thousand patients, or fewer than four thousand patients if any patients have multiple clinical decision points where the same disorder was treated), and one thousand of those data rows indicate a particular treatment was selected. Suppose further that five hundred of those one thousand rows indicate a positive outcome (e.g., abatement of the symptoms or management of the disorder). In such an example, the Treatment Analyzer 150 will generate a result statistic indicating that for patients within the precision cohort who were treated with the particular treatment, fifty percent of them saw positive results.

Finally, as illustrated by block 305, the Treatment Application 130 generates the personalized treatment options. In one embodiment, the personalized treatment options may include potential outcomes and distributional statistics for each outcome, such as an indication as to the generated result statistic for each treatment option. For example, the Treatment Application 130 may provide personalized results such as "650 similar patients took beta-blocker medications and 65% of them were able to achieve blood pressure control after 6 months," or "500 similar patients took Thiazide diuretics and 55% of them were able to achieve blood pressure control after 6 months." In some embodiments, the treatment options may be sorted or filtered based on the generated results statistics. In some embodiments, the Treatment Application 130 selects a treatment option based on the generated statistics. In a related embodiment, a healthcare provider may reject or accept this treatment suggestion. Notably, in embodiments, the personalized treatment options may include the treatment that the patient is already receiving. In such an embodiment, the best option may be to continue the current treatment. In this way, the Treatment Application 130 provides a highly personalized analysis of the treatment options and their predicted efficacy, which helps to ensure more efficient and high quality healthcare.

Figure 4:
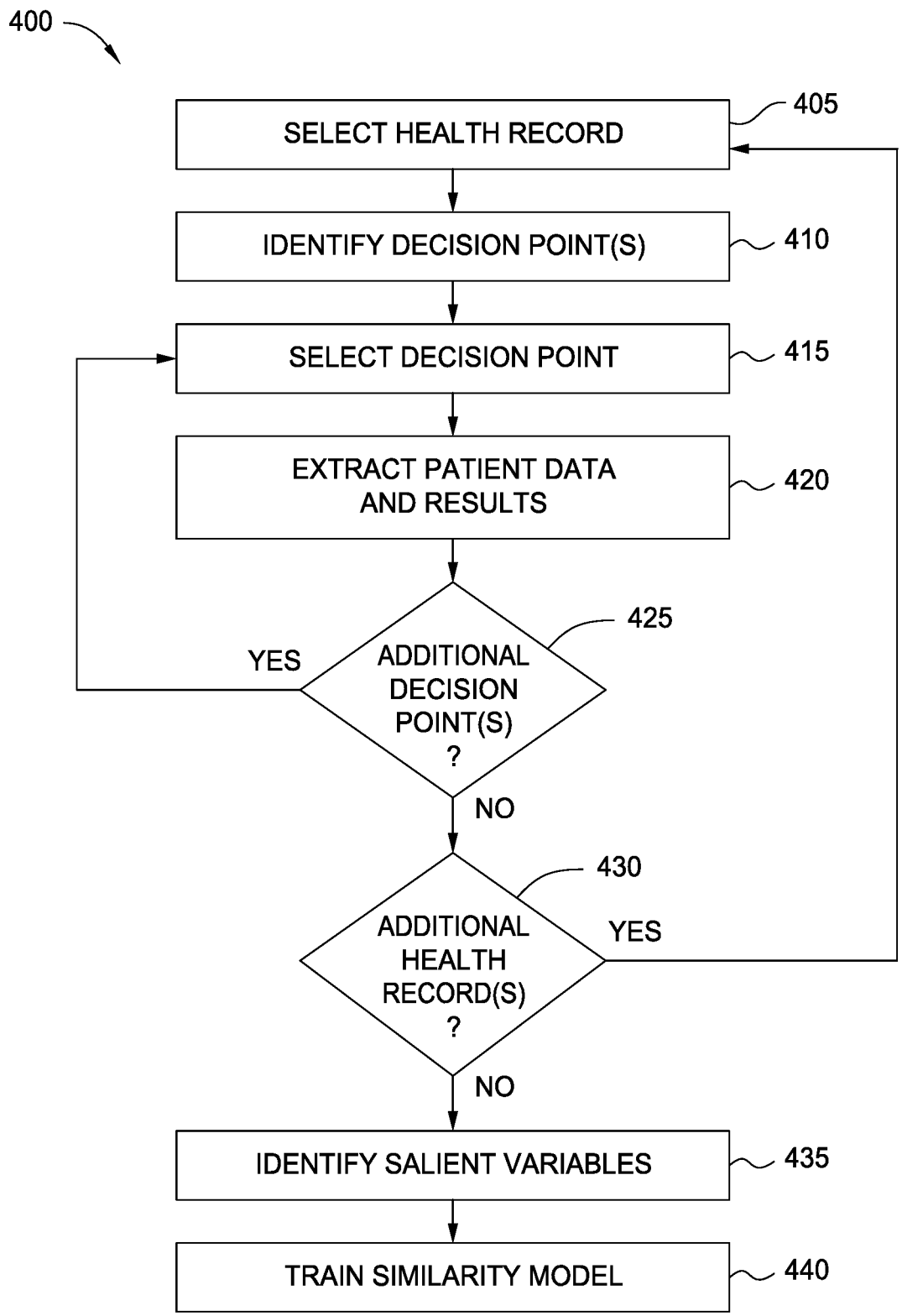
FIG. 4 is a flow diagram illustrating a method of training a similarity model for generating personalized treatments, according to one embodiment disclosed herein.

FIG. 4 is a flow diagram illustrating a Method 400 of training a Similarity Model 170 for generating personalized treatments, according to one embodiment disclosed herein. In some embodiments, the method 400 is performed separately for each disorder such that a unique Similarity Model 170 can be generated for each disorder. The method 400 begins at block 405, where the Extraction Component 135 selects a first Electronic Health Record 165. At block 410, the Extraction Component 135 identifies one or more clinical decision points in the Electronic Health Record 165. For example, as discussed above, a clinical decision point generally refers to a moment in time where a healthcare provider made a decision regarding treatment of a disorder. At block 415, the Extraction Component 135 selects a first decision point, and at block 420, the Extraction Component 135 extracts the patient data (e.g., attributes), the treatment option selected at that time, and results/outcome corresponding to the selected decision point.

The method 400 then proceeds to block 425, where the Extraction Component 135 determines whether there are additional decision points identified in the selected health record. If so, the method 400 returns to block 415 to select the next decision point. If not, the method 400 proceeds to block 430, where the Extraction Component 135 determines whether there are additional health records to be parsed. If so, the method 400 returns to block 405. Otherwise, the method 400 continues to block 435. Although not illustrated, in embodiments, the Extraction Component 135 also extracts guideline variables from each of the treatment guidelines. At block 435, the Extraction Component 135 identifies the salient variables, such as using one or more feature selection methods. Finally, at block 440, the Training Component 140 trains a similarity model based on the variables. As discussed above, in some embodiments, the Electronic Health Records 165 are pre-sorted such that only records corresponding to a particular disorder are processed. In some embodiments, as part of the method 400, the Extraction Component 135 determines which disorder(s) the identified decision points are associated with, and proceeds accordingly (i.e., by labeling each decision point with the corresponding disorder, and training the similarity model(s) based only on the decision points associated with the appropriate disorder).

Figure 5:
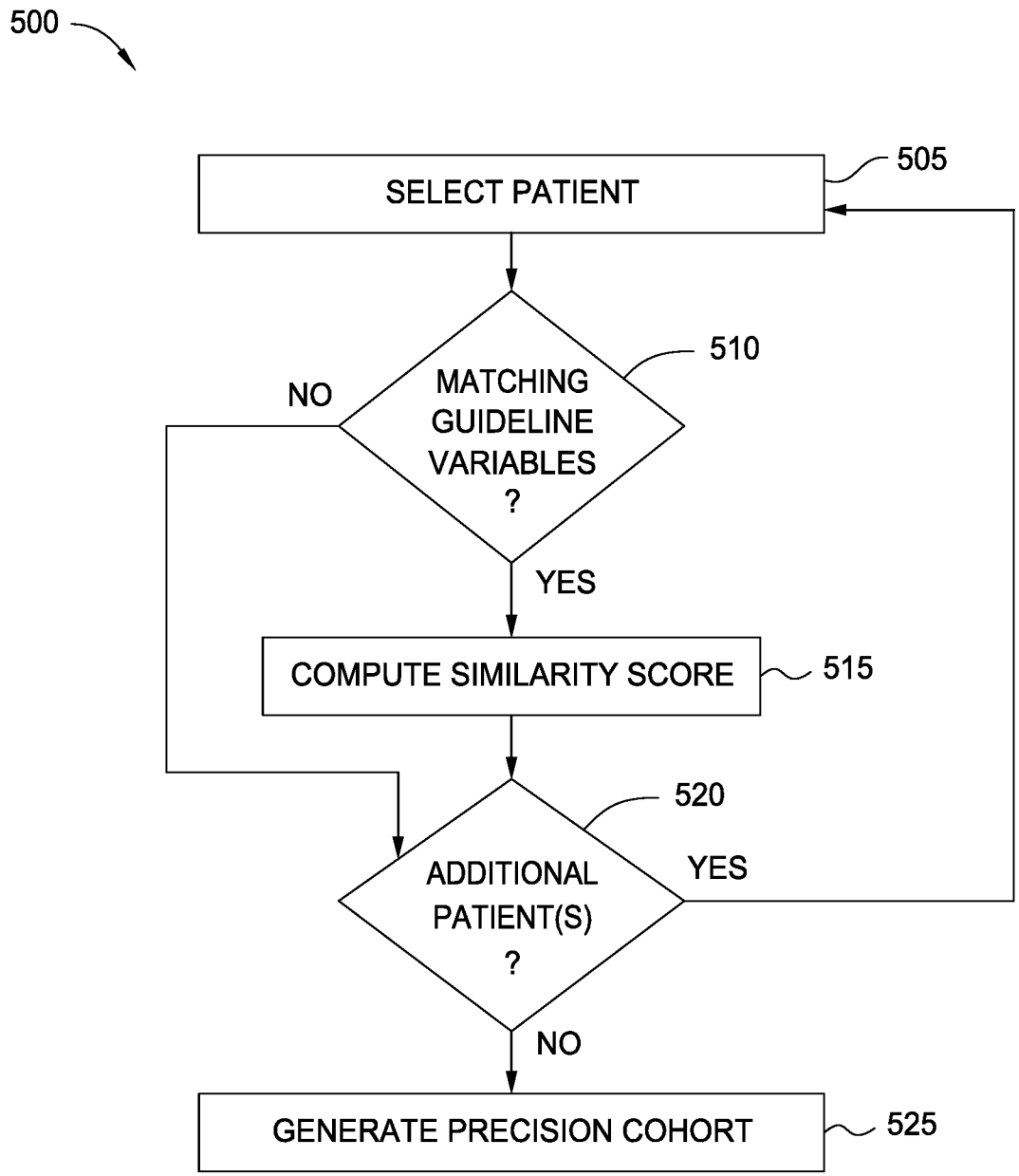
FIG. 5 is a flow diagram illustrating a method of generating precision cohorts, according to one embodiment disclosed herein.

FIG. 5 is a flow diagram illustrating a method 500 of generating precision cohorts, according to one embodiment disclosed herein. The method 500 begins at block 505, where a patient (or row) in the Scoring Dataset 245 is selected. As discussed above, in an embodiment, each row in the Scoring Dataset 245 corresponds to a particular clinical decision point, and a single patient may be represented in multiple rows. At block 510, the Cohort Generator 145 determines whether the selected row data matches the index patient's data with respect to the identified guideline variables. If not, the method 500 continues to block 520 to determine whether additional rows/patients remain in the dataset. If the data is aligned, however, the method 500 proceeds to block 515, where the Cohort Generator 145 computes a similarity score for the selected patient/row, based on the similarity model discussed above. At block 520, the Cohort Generator 145 determines whether there are additional patients/rows to be processed. If so, the method 500 returns to block 505 to select the next data. Otherwise, the method 500 proceeds to block 525, where the Cohort Generator 145 generates the precision cohort. For example, as discussed above, the precision cohort may be based on a subset of the rows of data (or patients) with the highest similarity scores.

Notably, in embodiments disclosed herein, two patients that have identical guideline variables may have significantly different precision cohorts generated, and thus the resulting personalized treatment outcomes may be significantly different. For example, suppose a treatment X has guidelines indicating that patients should be over the age of 60, should not smoke, and should have normal blood pressure. Suppose further that a Patient A is 63, does not smoke, has normal blood pressure, and has a BMI that is "overweight," while a Patient B is also 63, does not smoke, has normal blood pressure, and has a BMI that is "obese." Based on the guideline variables, Patient A and Patient B are identical: both are over 60, neither smoke, and both have normal blood pressure. However, the generated precision cohort for each is likely to be different because of the other attributes identified in their respective data, such as the fact that Patient A is overweight while Patient B is obese. Based on these different precision cohorts, the expected efficacy of the treatment X will be different. As such, even though the guidelines associated with treatment X do not indicate that the weight of the patient is relevant, the resulting personalized treatment options for each of Patient A and Patient B will differ based on this attribute, leading to different personalized treatments for each.

Figure 6:
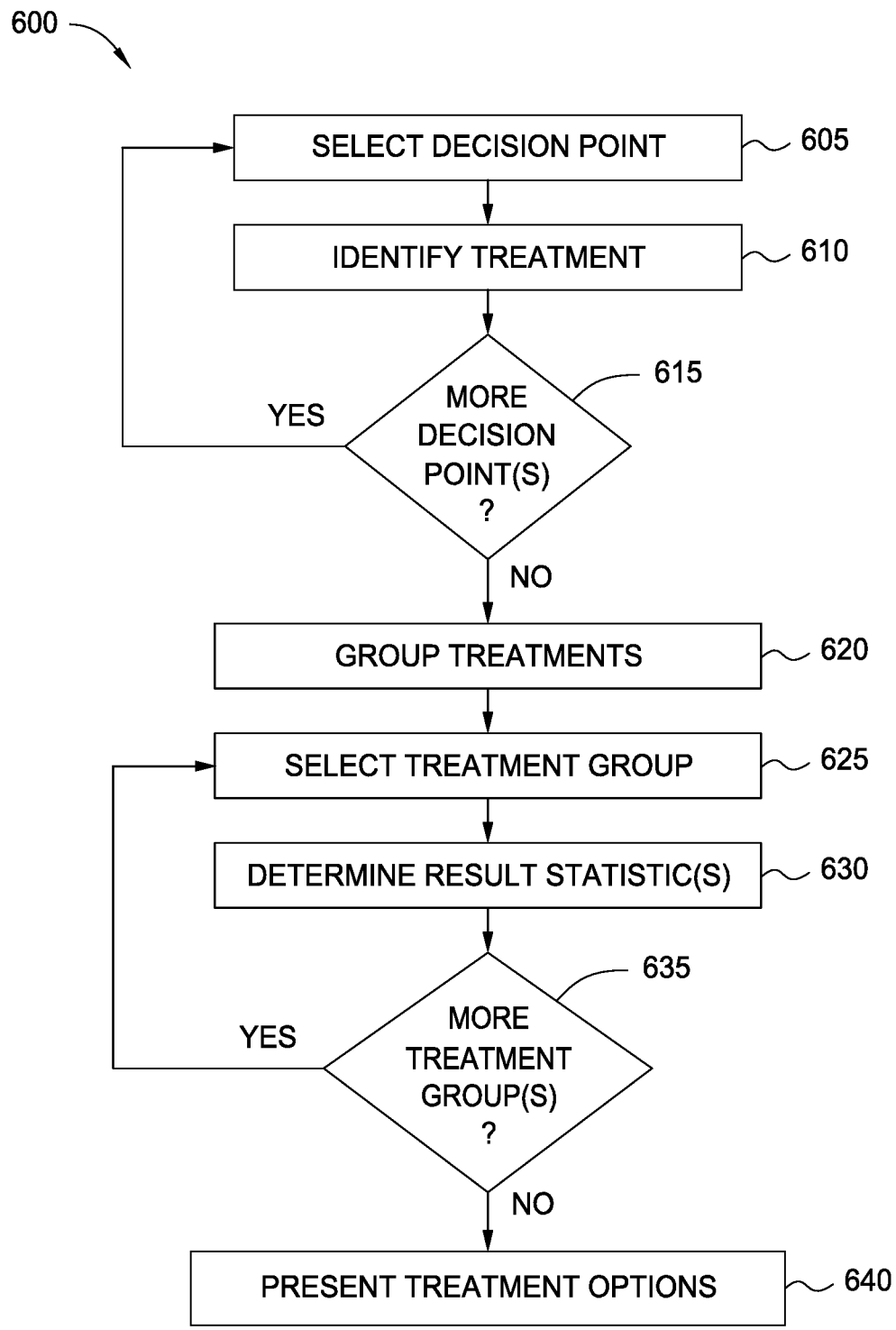
FIG. 6 is a flow diagram illustrating a method of generating personalized treatment options, according to one embodiment disclosed herein.

FIG. 6 is a flow diagram illustrating a method 600 of generating personalized treatment options, according to one embodiment disclosed herein. The method 600 begins at block 605, where the Treatment Analyzer 150 selects a first row in the precision cohort. That is, as discussed above, each row of data in the Scoring Dataset 245 and precision cohort may correspond to a particular clinical decision point related to the disorder that is being considered. Similarly, as discussed above, in some embodiments, each patient may contribute multiple rows of data to the Scoring Dataset 245 or precision cohort, because their records include multiple relevant decision points. At block 610, the Treatment Analyzer 150 identifies the treatment selected at the decision point. The method 600 then continues to block 615, where the Treatment Analyzer 150 determines whether there are additional decision point(s) in the precision cohort. If so, the method 600 returns to block 605. Otherwise, the method 600 proceeds to block 620.

At block 620, the Treatment Analyzer 150 separates the decision points into groups based on the selected treatment option. For example, decision points where the healthcare provider prescribed a first medication will be assigned to a first group, while points where the provider prescribed a second medication are assigned to a second group. Similarly, in some embodiments, one or more groups may include multiple treatments, such as if the healthcare provider prescribed two medications, included a recommended diet, and the like. At block 625, the Treatment Analyzer 150 selects a first treatment group for processing. The method 600 then continues to block 630, where the Treatment Analyzer 150 determines one or more result statistics for the treatment group. For example, as discussed above, the Treatment Analyzer 150 may determine what percentage of patients receiving the respective treatment saw a change in their disorder using the treatment option, the magnitude and direction of those changes, the timeline of the changes, and the like.

At block 635, the Treatment Analyzer 150 determines whether there are additional treatment groups to be analyzed. That is, the Treatment Analyzer 150 determines whether there are any treatment options identified in the precision cohort that have not yet been processed. If so, the method 600 returns to block 625 to select the next group. Otherwise, the method 600 proceeds to block 640, where the Treatment Analyzer 150 generates and presents the personalized treatment options. For example, as discussed above, the Treatment Analyzer 150 may rank, sort, or filter the options in various ways based on the determined outcome statistics.

FIG. 7 is a flow diagram illustrating a method 700 of generating personalized treatment options, according to one embodiment disclosed herein. At block 705, the Training Application 130 extracts a plurality of attributes from a plurality of electronic health records, wherein each electronic health record is associated with a patient in a plurality of patients. The method 700 then proceeds to block 710, where the Training Application 130 generates a training data set and a scoring data set based on the plurality of attributes. At block 715, the Training Application 130 trains a patient similarity model based on the training data set. The method 700 continues to block 720, where the Training Application 130 identifies a precision cohort of patients in the plurality of patients that are similar to a first patient based on an electronic health record of the first patient and the similarity model. At block 725, the Training Application 130 determines at least one result statistic for each of a plurality of treatments given to patients in the precision cohort. Finally, the method 700 concludes at block 730, where the Training Application 130 selects a first treatment of the plurality of treatments for the first patient based at least in part on the determined result statistics. For example, as discussed above, the Training Application 130 may select the treatment plan(s) corresponding to result statistics indicating the highest probability of recovery.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Treatment Application 130) or related data available in the cloud. For example, the Treatment Application 130 could execute on a computing system in the cloud and generate personalized treatment options. In such a case, the Treatment Application 130 could generate precision cohorts and store similarity models at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
    extracting a plurality of attributes from a plurality of electronic health records, wherein each electronic health record is associated with a patient in a plurality of patients, comprising:
        identifying a first decision point in a first electronic health record of the plurality of electronic health records, wherein the first decision point corresponds to a patient attending an appointment with a healthcare provider; and
        extracting a treatment selected by the healthcare provider at the first decision point, wherein the selected treatment comprises a decision to continue a current treatment plan;
    generating a training data set based on the plurality of attributes without reference to an index patient;
    generating a scoring data set based on the plurality of attributes, wherein:
        the scoring data set and the training data set differs by at least one attribute;
        the scoring data set is updated upon new information becoming available, wherein the new information corresponds to a new patient; and the training data set is updated only periodically, such that the scoring data set is updated more frequently than the training data set, wherein the training data set includes:
    a first row with information corresponding to a first healthcare encounter by a first patient,
    a second row with information corresponding to a second healthcare encounter by the first patient, and
    a third row with information corresponding to a first healthcare encounter by a second patient, and
    wherein the scoring data set includes at least a first variable that is excluded from the training data set;
training a patient similarity model based on the training data set using locally supervised metric learning (LSML) to learn a weight matrix that aligns similar patients more closely together, as compared to disparate patients, in a multidimensional vector space, wherein:
    the patient similarity model is specific to a first disorder, of a plurality of disorders, and
    the patient similarity model is updated periodically alongside the training data set;
identifying a precision cohort of patients in the plurality of patients in the scoring data set that are similar to the index patient based on an electronic health record of the index patient and the similarity model, comprising:
    prior to generating similarity scores, identifying a subset of the plurality of patients by filtering the plurality of patients based on one or more guideline variables and without use of the similarity model, wherein at least one of the one or more guideline variables specifies a numerical value for a biometric reading, and wherein a value of the biometric reading for each of the patients in the subset of the plurality of patients matches a value of the biometric reading for the index patient; and
    subsequent to identifying the subset of the plurality of patients, generating similarity scores for the patients in the subset of the plurality of patients using the similarity model;
determining at least one result statistic for each of a plurality of treatments given to patients in the precision cohort; and
selecting a first treatment of the plurality of treatments for the first disorder and the index patient based at least in part on the determined result statistics, comprising displaying the first variable to a healthcare provider, wherein the first variable is not used to affect selection, scoring, or filtering of the precision cohort.

2. The method of claim 1, wherein extracting the plurality of attributes comprises:
    identifying a plurality of decision points in each of the plurality of electronic health records;
    extracting one or more treatments selected at least one identified decision point;
    extracting one or more guideline variables associated with the one or more treatments; and
    extracting one or more results variables associated with at least one identified decision point.

3. The method of claim 2, wherein generating the training data set comprises identifying and selecting one or more salient variables from the plurality of attributes, the one or more guideline variables, and the one or more results variables using a feature selection model.

4. The method of claim 1, wherein training the patient similarity model comprises processing the training data set using one or more metric learning methods.

5. The method of claim 1, wherein training the patient similarity model further comprises processing the training data set using one or more clustering methods.

6. The method of claim 2, wherein identifying the precision cohort further comprises:
    identifying a first set of attributes that correspond to the one or more guideline variables and are exhibited by the index patient, based on the electronic health record of the index patient;
    identifying a group of patients in the plurality of patients with attributes matching the first set of attributes;
    generating a similarity score for each patient in the identified group of patients by processing each of the identified group of patients with the patient similarity model; and
    selecting one or more of the identified group of patients for inclusion in the precision cohort based on the generated similarity scores.

7. The method of claim 2, wherein determining at least one result statistic for each of a plurality of treatments comprises:
    generating one or more clusters of patients in the precision cohort based on a respective treatment in the plurality of treatments that each patient received;
    computing the at least one result statistic for each of the plurality of treatments based on the extracted one or more results variables for each patient in each of the one or more clusters.

8. A computer program product comprising a computer-readable storage medium having computer-readable program code embodied therewith, the computer-readable program code executable by one or more computer processors to perform an operation comprising:
    extracting a plurality of attributes from a plurality of electronic health records, wherein each electronic health record is associated with a patient in a plurality of patients, comprising:
        identifying a first decision point in a first electronic health record of the plurality of electronic health records, wherein the first decision point corresponds to a patient attending an appointment with a healthcare provider; and
        extracting a treatment selected by the healthcare provider at the first decision point, wherein the selected treatment comprises a decision to continue a current treatment plan;
    generating a training data set based on the plurality of attributes without reference to an index patient;
    generating a scoring data set based on the plurality of attributes, wherein:
        the scoring data set and the training data set differs by at least one attribute;
        the scoring data set is updated upon new information becoming available, wherein the new information corresponds to a new patient; and
        the training data set is updated only periodically, such that the scoring data set is updated more frequently than the training data set, wherein the training data set includes:
            a first row with information corresponding to a first healthcare encounter by a first patient,
            a second row with information corresponding to a second healthcare encounter by the first patient, and a third row with information corresponding to a first healthcare encounter by a second patient, and wherein the scoring data set includes at least a first variable that is excluded from the training data set;

training a patient similarity model based on the training data set using locally supervised metric learning (LSML) to learn a weight matrix that aligns similar patients more closely together, as compared to disparate patients, in a multidimensional vector space, wherein:

the patient similarity model is specific to a first disorder, of a plurality of disorders, and the patient similarity model is updated periodically alongside the training data set;

identifying a precision cohort of patients in the plurality of patients in the scoring data set that are similar to the index patient based on an electronic health record of the index patient and the similarity model, comprising:

prior to generating similarity scores, identifying a subset of the plurality of patients by filtering the plurality of patients based on one or more guideline variables and without use of the similarity model, wherein at least one of the one or more guideline variables specifies a numerical value for a biometric reading, and wherein a value of the biometric reading for each of the patients in the subset of the plurality of patients matches a value of the biometric reading for the index patient; and subsequent to identifying the subset of the plurality of patients, generating similarity scores for the patients in the subset of the plurality of patients using the similarity model;

determining at least one result statistic for each of a plurality of treatments given to patients in the precision cohort; and selecting a first treatment of the plurality of treatments for the first disorder and the index patient based at least in part on the determined result statistics, comprising displaying the first variable to a healthcare provider, wherein the first variable is not used to affect selection, scoring, or filtering of the precision cohort.

9. The computer program product of claim 8, wherein extracting the plurality of attributes comprises:

identifying a plurality of decision points in each of the plurality of electronic health records;

extracting one or more treatments selected at least one identified decision point;

extracting one or more guideline variables associated with the one or more treatments; and extracting one or more results variables associated with at least one identified decision point.

10. The computer program product of claim 9, wherein generating the training data set comprises identifying and selecting one or more salient variables from the plurality of attributes, the one or more guideline variables, and the one or more results variables using a feature selection model.

11. The computer program product of claim 8, wherein training the patient similarity model comprises processing the training data set using one or more metric learning methods.

12. The computer program product of claim 8, wherein training the patient similarity model further comprises processing the training data set using one or more clustering methods.

13. The computer program product of claim 9, wherein identifying the precision cohort further comprises:

identifying a first set of attributes that correspond to the one or more guideline variables and are exhibited by the index patient, based on the electronic health record of the index patient;

identifying a group of patients in the plurality of patients with attributes matching the first set of attributes;

generating a similarity score for each patient in the identified group of patients by processing each of the identified group of patients with the patient similarity model; and selecting one or more of the identified group of patients for inclusion in the precision cohort based on the generated similarity scores.

14. The computer program product of claim 9, wherein determining at least one result statistic for each of a plurality of treatments comprises:

generating one or more clusters of patients in the precision cohort based on a respective treatment in the plurality of treatments that each patient received;

computing the at least one result statistic for each of the plurality of treatments based on the extracted one or more results variables for each patient in each of the one or more clusters.

15. A system comprising:

one or more computer processors; and a memory containing a program which when executed by the one or more computer processors performs an operation, the operation comprising:

extracting a plurality of attributes from a plurality of electronic health records, wherein each electronic health record is associated with a patient in a plurality of patients, comprising:

identifying a first decision point in a first electronic health record of the plurality of electronic heath records, wherein the first decision point corresponds to a patient attending an appointment with a healthcare provider; and extracting a treatment selected by the healthcare provider at the first decision point, wherein the selected treatment comprises a decision to continue a current treatment plan;

generating a training data set based on the plurality of attributes without reference to an index patient;

generating a scoring data set based on the plurality of attributes, wherein:

the scoring data set and the training data set differs by at least one attribute;

the scoring data set is updated upon new information becoming available, wherein the new information corresponds to a new patient; and the training data set is updated only periodically, such that the scoring data set is updated more frequently than the training data set, wherein the training data set includes:

a first row with information corresponding to a first healthcare encounter by a first patient, a second row with information corresponding to a second healthcare encounter by the first patient, and a third row with information corresponding to a first healthcare encounter by a second patient, and wherein the scoring data set includes at least a first variable that is excluded from the training data set;

training a patient similarity model based on the training data set using locally supervised metric learning (LSML) to learn a weight matrix that aligns similar patients more closely together, as compared to disparate patients, in a multidimensional vector space, wherein:
  the patient similarity model is specific to a first disorder, of a plurality of disorders, and
  the patient similarity model is updated periodically alongside the training data set;
identifying a precision cohort of patients in the plurality of patients in the scoring data set that are similar to the index patient based on an electronic health record of the index patient and the similarity model, comprising:
  prior to generating similarity scores, identifying a subset of the plurality of patients by filtering the plurality of patients based on one or more guideline variables and without use of the similarity model, wherein at least one of the one or more guideline variables specifies a numerical value for a biometric reading, and wherein a value of the biometric reading for each of the patients in the subset of the plurality of patients matches a value of the biometric reading for the index patient; and
  subsequent to identifying the subset of the plurality of patients, generating similarity scores for the patients in the subset of the plurality of patients using the similarity model;
determining at least one result statistic for each of a plurality of treatments given to patients in the precision cohort; and
selecting a first treatment of the plurality of treatments for the first disorder and the index patient based at least in part on the determined result statistics, comprising displaying the first variable to a healthcare provider, wherein the first variable is not used to affect selection, scoring, or filtering of the precision cohort.

16. The system of claim 15, wherein extracting the plurality of attributes comprises:
  identifying a plurality of decision points in each of the plurality of electronic health records;
  extracting one or more treatments selected at least one identified decision point;
  extracting one or more guideline variables associated with the one or more treatments; and
  extracting one or more results variables associated with at least one identified decision point.

17. The system of claim 16, wherein generating the training data set comprises identifying and selecting one or more salient variables from the plurality of attributes, the one or more guideline variables, and the one or more results variables using a feature selection model.

18. The system of claim 15, wherein training the patient similarity model comprises processing the training data set using one or more metric learning methods.

19. The system of claim 16, wherein identifying the precision cohort further comprises:
  identifying a first set of attributes that correspond to the one or more guideline variables and are exhibited by the index patient, based on the electronic health record of the index patient;
  identifying a group of patients in the plurality of patients with attributes matching the first set of attributes;
  generating a similarity score for each patient in the identified group of patients by processing each of the identified group of patients with the patient similarity model; and
  selecting one or more of the identified group of patients for inclusion in the precision cohort based on the generated similarity scores.

20. The system of claim 16, wherein determining at least one result statistic for each of a plurality of treatments comprises:
  generating one or more clusters of patients in the precision cohort based on a respective treatment in the plurality of treatments that each patient received;
  computing the at least one result statistic for each of the plurality of treatments based on the extracted one or more results variables for each patient in each of the one or more clusters.

* * * * *